(12) United States Patent
Walsdorf et al.

(10) Patent No.: US 6,818,228 B1
(45) Date of Patent: Nov. 16, 2004

(54) DIETARY SUPPLEMENTS CONTAINING ULTRADENSE CALCIUM CITRATE AND CARBONYL IRON

(75) Inventors: Neill B. Walsdorf, San Antonio, TX (US); Cindy L. Wabner, Canyon Lake, TX (US); George Alexandrides, San Antonio, TX (US)

(73) Assignee: Mission Pharmacal Company, San Antonio, TX (US)

( * ) Notice: Subject to any disclaimer, the term of this patent is extended or adjusted under 35 U.S.C. 154(b) by 0 days.

(21) Appl. No.: 08/667,503

(22) Filed: Jun. 21, 1996

(51) Int. Cl.⁷ ............................. A61K 9/20; A61K 33/26
(52) U.S. Cl. ....................... 424/464; 424/646; 424/647; 424/648; 514/904; 514/905
(58) Field of Search ................................. 514/574, 905, 514/904; 424/646, 647, 648

(56) References Cited

U.S. PATENT DOCUMENTS

| | | | |
|---|---|---|---|
| 4,431,634 A | 2/1984 | Ellenbogen | |
| 4,772,467 A | 9/1988 | Pak | |
| 4,814,177 A | * 3/1989 | Walsdorf et al. | ............ 424/464 |
| 4,851,221 A | 7/1989 | Pak et al. | |
| 4,895,980 A | 1/1990 | Walsdorf et al. | |
| 4,985,593 A | 1/1991 | Walsdorf et al. | |
| 5,075,499 A | 12/1991 | Walsdorf et al. | |
| 5,219,889 A | 6/1993 | Walsdorf et al. | |
| 5,432,200 A | 7/1995 | Walsdorf et al. | |
| 5,494,678 A | 2/1996 | Paradissis et al. | .......... 424/439 |

FOREIGN PATENT DOCUMENTS

| | | |
|---|---|---|
| EP | 0702954 A2 | 3/1996 |
| WO | 95/35098 | * 12/1995 |

OTHER PUBLICATIONS

Bock Pharmacal Company marketing brochure for "Prenate 90" tablets published Oct. 1994.*
Bronson labeling and product information for "Prenatal II" tablets, 1996.*
International Search Report mailed Oct. 30, 1997.
Bock Pharmacal Company marketing brochure for "Prenate 90®" tablets published Oct. 1994. Prenate 90® was first offered for sale Jun. 27, 1980.
Bronson labeling and product information for "Prenatal II" tablets, weight management products, vitamins and herbals, Winter/Spring 1996.
Lederle Laboratories product information for "Materna® Prenatal Vitamin and Mineral Tablets," 1988.
"Food and Nutrition Board, National Academy of Sciences—National Research Counsel Recommended Dietary Allowances," Rev. 1989.
"Comments on Lower Toxicity of Carbonyl Iron," presented to the FDA Public Workshop on Acute Toxicity of Elemental Forms of Iron Relative to That of Iron Salts, *International Speciality Products,* Wayne, New Jersey, Apr. 20, 1995.
"Nutrition During Pregnancy," cover page, copyright page and pp. 238–257, 263, 272–335, National Academy Press, 1990.

* cited by examiner

*Primary Examiner*—Barbara P. Badio
(74) *Attorney, Agent, or Firm*—Fulbright & Jaworski L.L.P.

(57) ABSTRACT

A vitamin and mineral supplement containing ULTRADENSE™ calcium citrate and carbonyl iron for use in humans. Calcium in the form of citrate enhances absorption of iron, zinc, and magnesium. ULTRADENSE™ calcium citrate provides more bioavailable calcium than usual preparations of calcium citrate. Carbonyl iron provides iron in a form that significantly reduces the risk to children of accidental iron poisoning from formulations that provide iron in salt form. The supplement may further contain a number of vitamins and minerals in a tablet that is elegantly small, weighing about 1.5–1.6 g. The small size allows ease of swallowing and encourages patient acceptability. Methods of making such a supplement and methods of treating maladies in need of vitamin and mineral supplementation are provided.

22 Claims, 3 Drawing Sheets

US 6,818,228 B1

DIETARY SUPPLEMENTS CONTAINING ULTRADENSE CALCIUM CITRATE AND CARBONYL IRON

FIELD OF THE INVENTION

The present invention relates generally to the fields of nutrition and obstetrics. More particularly, the present invention relates to a dietary supplement for use in humans, and in particular, in pregnant or lactating women, which supplement comprises calcium citrate and carbonyl iron. Compositions and methods for enhancing uptake of calcium, zinc, magnesium, or iron for a human are also provided.

BACKGROUND OF THE INVENTION

Vitamin and mineral compositions are commonly taken as dietary aids either as therapeutic preparations directed to a specific medical problem or as general nutritional supplements. Daily requirements for vitamins and minerals vary depending upon such factors as sex, body size, growth rate, exercise, disease, and age. Such compositions are especially provided for pregnant or lactating women to ensure provision of adequate nutrients for the developing fetus and for the mother.

Supplements pose a potential problem of nutrient—nutrient interactions. An excess of one nutrient in a supplement may interact with another nutrient in the supplement, thereby affecting absorption adversely, or less often, beneficially. For example, iron is reported to inhibit the absorption of zinc (Hambridge et al., *Obstet. Gynecol.* 4:593–596, 1987), zinc is reported to inhibit the absorption of copper (Festa et al., *Am. J. Clin. Nutr.* 41:285–292, 1985), calcium is reported to interfere with the absorption of both iron and zinc (Seligman et al., *Obstet. Gynecol.* 61:356–362, 1983), and protein is reported to increase urinary calcium losses (Allen et al., *Am. J. Clin. Nutr.* 32:741–749, 1979) and vitamin B6 requirements (National Research Council, Recommended Dietary Allowances, 10th ed., Natl. Acad. Press, Washington, D.C. 1989)

Calcium is required for adequate bone formation and maintenance, as well as for diverse metabolic functions. Approximately 99% of the calcium in the human body is located in the skeleton. Women are advised to increase their calcium intake substantially during pregnancy, and concern exists regarding many pregnant women who do not ingest enough calcium to maintain their own skeletons while providing for fetal needs. An estimated 600–800 mg of calcium is ingested in an average diet, far below the recommended dietary allowance. The efficiency of calcium absorption is determined by several factors, including the chemical form of ingested calcium. Part of the absorbed calcium is eliminated in urine, which poses a problem for certain people who are prone to the formation of calcium-containing kidney stones.

Ingested calcium is absorbed across the wall of the gastrointestinal tract and, in particular, the upper small intestine. To be absorbed across the intestinal wall, calcium must be soluble as an ionized form or as a salt form. Two major factors affect the amount of soluble calcium in the gastrointestinal tract. The first factor is gastric acid secretion, which increases the solubility of calcium by lowering the pH of intestinal fluids. This is important because ingested calcium is typically in the form of relatively insoluble salts, such as calcium carbonate and calcium phosphate. The second factor determining calcium absorption is the secretion of bicarbonate from the pancreas into the small intestine. The bicarbonate secreted into the small intestine alkalinizes fluid contained in the intestine, thereby decreasing the solubility of calcium. The absorption of calcium from the small intestine under a number of conditions varies with the form of ingested calcium salt. Minerals such as zinc and iron also depend upon stomach acid to become solubilized for intestinal absorption. Calcium in the form of calcium carbonate decreases the absorption of those minerals because of neutralization of the acidic environment.

Intestinal calcium absorption was reported to be increased almost 25% in women when the calcium was administered in the form of calcium citrate as compared to calcium carbonate (Harvey et al., *J. Am. Coll. of Nutr.,* 9(6):583–587, 1990.) In another study, performed in healthy, postmenopausal women, supplementation with calcium citrate was reported to be more effective than supplementation with equimolar amounts of calcium carbonate (Dossen-Use et al., *N. Eng. J. Med.,* 323:878–83, 1990.) In patients with decreased gastric acid secretion, intestinal calcium absorption was reportedly ten-fold higher when calcium was administrated as a citrate salt as compared to a bicarbonate salt (Recker et. al., *N. Eng. J. Med.,* 313:70–73, 1965.) Despite the higher intestinal absorption of calcium when administered in the form of calcium citrate, the use of calcium citrate actually was reported to decrease the propensity for the crystallization of calcium oxalate in the urine (Harvey et al., *J. Clin. Endocrin. and Metab.,* 61(6): 1225–1233.

Calcium citrate is an efficiently absorbable chemical form of calcium. Because of improved absorption of calcium, osteoporosis development is precluded. Citrate is a known inhibitor of calcium stone formation, therefore, the risk of calcium nephrolithiasis (resulting from calcium supplementation) is reduced. An especially dense form of calcium citrate having advantageous properties regarding solubility and bioavailability is ULTRADENSE™ calcium citrate as described in U.S. Pat. Nos. 4,814,177; 4,851,221; and 4,772,467, incorporated by reference herein, and marketed under the tradename CITRACAL®. CITRACAL® with vitamin D is also available.

Accidental overdoses of iron-containing supplements are the most common cause of poisoning death in children under six. The FDA, Consumer Product Safety Commission, and American Association of Poison Control Centers are actively developing new regulations seeking to correct this significant public health issue which has seen the number of reported accidental iron ingestions in children more than double, to over 110,000, in the last decade.

Safety of iron supplements is a significant public health issue. Since 1986 at least 38 children between the ages of 9 months and 3 years have died from accidental ingestion of iron supplement products according to the American Association of Poison Control Centers. Over this same time frame, the FDA has recorded more than 110,000 incidents of pediatric iron overdose, and iron poisoning has become the number one cause of poisoning death in children. Ferrous salts, commonly used in prenatal vitamin preparations, can produce toxic symptoms at ingestion levels as low as 25 mg/kg and significant iron poisoning at levels as low as 60 mg/kg.

Alternatively, elemental iron may be supplied in a supplement as carbonyl iron. The term "carbonyl iron" is from a manufacturing process in which gaseous iron pentacarbonyl is heated under controlled conditions to extremely high temperatures resulting in the deposition of submicroscopic particles of 98% pure elemental iron that aggregate into spheres having a diameter of from about 2–8 microns (average of 5 microns). The importance of the small size is that carbonyl iron particles have very large surface areas since this property varies inversely with the size of a particle. The larger surface area results in higher reactivity of carbonyl iron particles with gastric acid in the stomach and consequently higher absorption rates. Thus, carbonyl iron exhibits 2–5 times higher bioavailability than other elemental iron forms (Sacks and Houchin, *Am. J. Clin. Nutr.* 31:566–571, 1978). Studies in laboratory animals and humans show that carbonyl iron is as well absorbed as ferrous sulfate and ferrous fumarate without the attendant risk of iron toxicity. Carbonyl iron has been marketed under the name FERRONYL® IRON.

Within the stomach, carbonyl iron is oxidized to the ferrous form of iron using naturally produced stomach acids. This provides a delayed-release mechanism regulated by the body's own acid secretion. Because of its natural, self-regulated delayed release, carbonyl iron is significantly safer than other ferrous iron salts used in ordinary prenatal vitamins. In animal studies, carbonyl iron had an $LD_0$ (the dose where all animals survive) of 10,000 to 15,000 mg/kg of iron, and an $LD_{100}$ (the dose where all animals died) of 50,000 to 60,000 mg/kg of iron (Shelanski, *Bull Nat Formulary Committee*, 1980, 18:87–94). This represents a level of safety at least 100 times higher than traditional ferrous salts, with a therapeutic profile that is similar to that of ferrous salts. Iron replenishment studies in human subjects using doses of carbonyl iron up to 3,000 mg daily (approximately 15 times the usual dose of ferrous sulfate iron) have confirmed this remarkable safety profile (Gordeuk et al., *Blood*, 1986; 67:745–752).

Iron supplementation can produce epigastric distress. In studies with female blood donors using doses of carbonyl iron 10 times higher than normal doses of ferrous sulfate, the incidence of gastrointestinal side effects was equivalent (Gordeuk et al., *Am J Clin Nutr*, 1987; 46:1029–1034). The iron needs of females who donate blood more than three times a year are believed to closely mimic the iron needs during pregnancy. The ability to tolerate significantly higher doses of carbonyl iron in these blood donors lead to faster restoration of iron stores. Even at extremely high doses of carbonyl iron, there have been no reports of iron overload.

EP publication EP 0702954 relates to a calcium dietary supplement comprising a calcium salt, vitamin D and at least one mineral; where the calcium salt may be calcium citrate. Bronson Vitamins and Herbals (Winter/Spring 1996 catalog) describes a prenatal II (or #2) supplement that contains 125 mg of calcium (citrate) and 30 mg of iron (FERRONYL®). Calcium at a level of 125 mg is only 10% of the recommended dietary allowance for pregnant or lactating women.

Because of the above difficulties with safety regarding iron supplements, undesired interactions in competing for stomach acid, and use of suboptimal forms of calcium, the present inventors provide herein an improved single oral dosage supplement that contains unprecedented levels of calcium in a form that is ready solubilized in vivo, together with carbonyl iron to provide a safe and effective dietary supplement. Further vitamins and minerals can be included and, when included, provides a single oral dosage form containing calcium, iron and the recommended dietary allowance of a number of vitamins and minerals in a tablet that is small enough for easy swallowing, thereby, encouraging patient acceptance. Further advantages will become apparent in this disclosure.

SUMMARY OF THE INVENTION

The present invention provides a dietary supplement comprising calcium citrate and carbonyl iron. ULTRADENSE™ calcium citrate provides a greater amount of calcium in a form that enhances absorption of iron, zinc, and magnesium compared to usual calcium citrate; and uses carbonyl iron to provide iron in a form that significantly reduces the risk to children of accidental iron poisoning from formulations that provide iron in salt form. A further supplement of the invention comprises iodine; zinc; folic acid; copper; vitamins A, D, E, C, B1, B2, B6, B12; and niacinamide.

A calcium citrate composition having a bulk density between 0.8 g/cc and 1.3 g/cc, preferably between 1.05 g/cc and 1.25 g/cc and most preferably between about 1.1 g/cc and 1.2 g/cc may be produced by methods of the present invention. Citric acid and a calcium compound selected from the group consisting of calcium carbonate, calcium oxide and calcium hydroxide are mixed to produce a mixture having a calcium compound/citric acid molar ratio of about 1.5. A hydrated mixture with a moisture content between about 30.5 weight percent and about 47.5 weight percent is produced by agitatively adding water to the mixture, although when desired the calcium compound, citric acid and water may be mixed in one step. The hydrated mixture is then blended to facilitate the reaction of citric acid with the calcium compound and to form a granulated mass primarily consisting of granules with diameters between about 1/64 inch and about 1/16 inch.

The granulated mass is then dried to a moisture content of between about 10 weight percent and about 13 weight percent to produce a calcium citrate composition having a bulk density greater than about 1.1 g/cc.

Calcium citrate tablets formed as described herein are generally greater than about 15 weight percent calcium and most usually have a calcium/citrate molar ratio of about 3/2. Such tablets preferably have a density greater than about 1.5 g/cc and may, for aesthetic or other purposes, be coated by conventional means with mixtures comprising substances such as sugar, polyvinylpyrrolidone, calcium carbonate and titanium dioxide, for example.

In a further embodiment of the invention, the supplement takes advantage of the density of ULTRADENSE™ calcium citrate and the tablet space saved by using carbonyl iron to provide a single oral tablet dosage form having the following minerals and vitamins: iodine; zinc; copper, folic acid; vitamins A, D, E, C, B1, B2, B6, B12; and niacinamide. The tablet also has the elegance of small size, weighing less than about 1.6 g, and consequent patient acceptability.

A vitamin and mineral dietary supplement comprising calcium citrate wherein the calcium citrate provides from about 100 to 300 mg calcium, carbonyl iron wherein the carbonyl iron provides from about 30 to 120 mg iron, and a vitamin is a further embodiment of the invention. A particularly preferred embodiment is a vitamin and mineral dietary supplement comprising calcium citrate, carbonyl iron, vitamin A, vitamin B1, vitamin B2, vitamin B6, vitamin B12, vitamin C, vitamin D, vitamin E, folic acid, iodine, copper, zinc, and niacinamide. The supplement also may comprise pharmaceutically acceptable carriers and excipients.

A method of making a vitamin and mineral dietary supplement comprising calcium citrate, carbonyl iron, and a vitamin is a further aspect of the invention. The method comprises the steps of: i) granulating calcium citrate with a first granulating agent to form a first granular mixture; ii) granulating Vitamin E, docusate Na, zinc, copper, and carbonyl iron with a second granulating agent to form a second granular mixture; iii) blending the first mixture with the second mixture in a blender to form a first blend; iv) adding carbonyl iron, vitamin A, vitamin B1, vitamin B2, vitamin B6, vitamin B12, vitamin C, vitamin D, folic acid, iodine, and niacinamide to the first blend; v) blending the first blend and added ingredients to form a second blend; and vi) formulating the second blend into an oral dosage form. A composition of matter comprising the second blend made by the abovedescribed process is also an embodiment of the invention.

In this method, the granulating agents have the properties of providing cohesion to form a granular material that allows formation of tablets having optimal dissolution characteristics. Granulating agents include, but are not limited to, ethyl cellulose, povidone, polyethylene glycol, shellac, methylcellulose, hydroxypropylmethylcellulose, or the like. When the first granulating agent is ethyl cellulose, the ethyl cellulose is present in a ratio to calcium citrate of about 2:98. A preferred second granulating agent is povidone in alcohol. An important aspect of the invention is that the second blend has a bulk density of about 0.9 to 1.1 g/cc.

A method of treating a vitamin or mineral deficiency or anticipated deficiency of a human is a further aspect of the invention. The method comprises the steps of obtaining a vitamin and mineral supplement as provided herein, and administering the supplement to the human having a vitamin or mineral deficiency. In particular, the human is pregnant or lactating, the human is a blood donor, or the human is anemic. A particular advantage for pregnant women is that the supplement enhances uptake of magnesium from the diet; magnesium sulfate in bolus form has long been used for preventing premature labor. Example 3 provides data demonstrating the enhanced uptake of magnesium.

A method of enhancing uptake of calcium, magnesium, iron, or zinc in a human comprising the steps of obtaining a vitamin and mineral supplement as provided herein, and administering the supplement to the human in need of enhanced uptake of calcium, magnesium, iron or zinc is a further aspect of the invention.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

Figure 1:
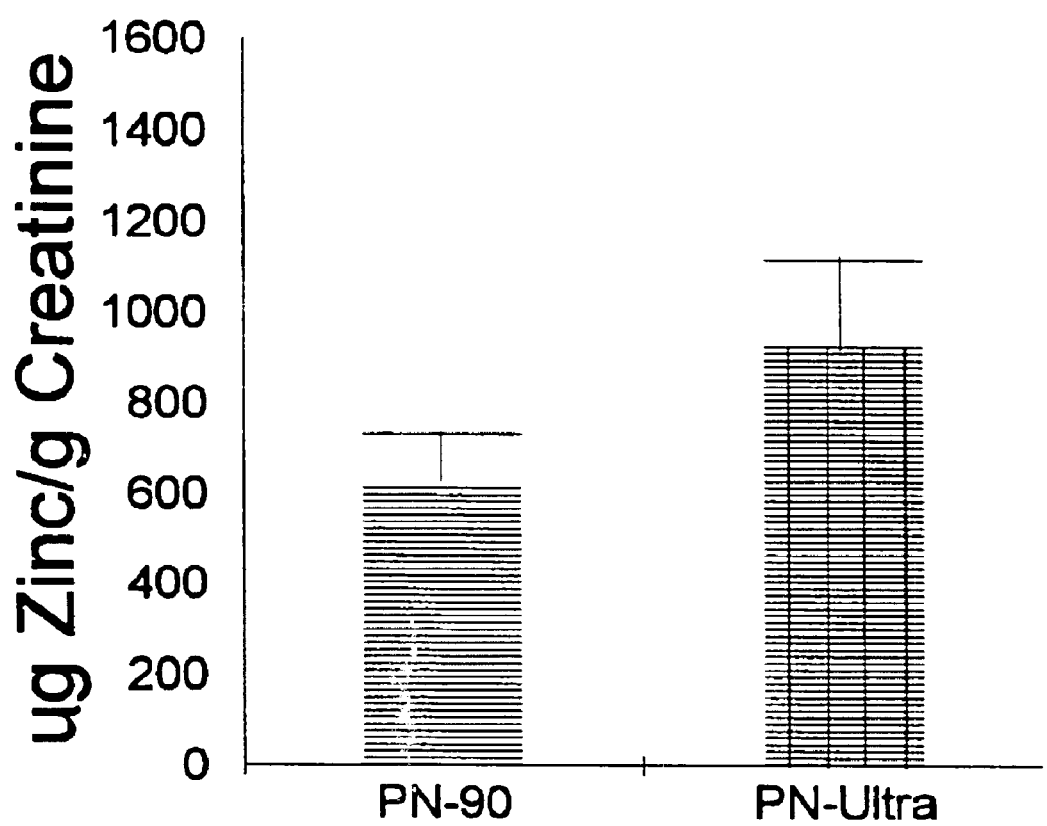
FIG. 1 provides a standard error analysis of data obtained from urine samples analyzed for zinc content after oral ingestion of either PRENATE® ULTRA™ (PN-Ultra) or PRENATE®90(PN-90). A significant difference of $p<0.03$ was found between the means of the two different supplements. Error bars represent standard error, n=9. See Example 3 for methods.

The present invention relates to the discovery that calcium citrate is a superior vehicle for dietary calcium supplementation. However, the ingestion of calcium citrate in a usual form presents potential problems. One potential problem, for example, is the bulkiness of usual calcium citrate which makes incorporating adequate amounts of calcium in a desired tablet size difficult. The present invention involves the discovery that exceedingly dense calcium citrate tablets may be made from bulk-form calcium citrate prepared in a particular fashion. The preferred fashion of bulk-form calcium citrate formulation comprises the reaction, in a dense hydrated mixture, of citric acid and a calcium compound selected from the group consisting of calcium carbonate, calcium oxide and calcium hydroxide. This dense hydrated mixture may be characterized as being a thick "slush" comprising calcium compound/citric acid combined in a molar ratio of about 3/2. The hydrated mixture has a preferable moisture content between about 30.5 weight percent and about 47.5 weight percent.

This hydrated mixture is blended, for example in a ribbon blender, until a granulated mass primarily consisting of granules with diameters between about 1/64 inch and about 1/16 inch is formed. The granulated mass is then dried to produce a calcium citrate composition having a moisture content between about 10 weight percent and about 13 weight percent, preferably about 12.6%. This calcium citrate composition has a bulk density (weight per gross volume) between about 0.80 g/cc and about 1.3 g/cc, preferably between 1.05 g/cc and 1.25 g/cc and more preferably between 1.1 g/cc and 1.2 g/cc. More extensive drying of the granulated mass with, for example, a fluid bed drier, may result in a calcium citrate composition unsuitable for the production of sufficiently dense calcium citrate tablets. Such an overly dried composition, having too little water and a bulk density less than about 0.80 S/cc, would be difficult to use for the production of dense calcium citrate tablets by the processes of the present invention.

Studies of surface area quantity and quality of calcium citrate composition of the present invention and of commercial calcium citrate tetrahydrate were performed. These surface area studies indicated that the commercial material was more porous and had much more surface area per unit of weight. The surface area per gram for the calcium citrate composition of the present invention was no more than about twenty percent of that found for commercial calcium citrate tetrahydrate. These surface area studies are also consistent with the more compressible nature of the calcium citrate composition of the present invention. The surface area range for the calcium citrate composition of the present invention is between about 0.7 $m^2/g$ and about 2.0 $m^2/g$, preferably between about 0.7 $m^2/g$ and about 0.80 $m^2/g$ and most preferably between about 0.75 $m^2/g$ and about 0.77 $m^2/g$. The upper surface area limit is less than about 2.0 $m^2/g$ and the preferred surface area limit is 1.0 $m^2/g$. Scanning electron microscopy of the calcium citrate composition of the present invention and of commercial calcium citrate tetrahydrate revealed that the latter was much more porous than the former. This observation was again consistent with the greater compactibility of the calcium citrate composition of the present invention.

Calcium carbonate (136 kg, 1356 moles) and powdered citric acid (174 kg, 906 moles) were placed in a PK Gardner 28 cu. ft. ribbon mixer and blended for about 5 minutes. Hot water (120 L, 40° C.) was added rapidly at first and then at a reduced rate as frothing ensued until all 120 L was added.

Blending in the ribbon mixer was continued until the material began to appear solid, white and granular. At this point 2-propanol (16 L) was subjoined to the solid, white granular appearing mixture to assist in granulation. The blending was then continued until the granules of the granulated mass appeared to have diameters between about 1/64 inch and about 1/16 inch. Further blending would produce granules larger than 1/16 inch which are preferably avoided for ease of later drying, mixing and tableting.

The granulated mass was then removed from the blender and placed on drying trays in layers about 3/4 inch thick. The granulated mass was then dried at a temperature of about 165° F. until the moisture content was between about 10% and about 13% to produce a dried calcium citrate composition with a bulk density greater than about 1.1 g/cc and usually less than about 1.25 g/cc.

Bulk density was measured by placing a weighed amount of calcium citrate composition in a volumetrically graduated 25 ml cylinder and tapping the cylinder until a constant volume was reached. The weight per unit volume was then calculated. True densities of calcium citrate preparations were measured by the displacement of helium gas by preweighed amounts, using a Micrometrics Model 1320 AutoPycnometer. A density value between about 2.4 g/cc and about 2.5 g/cc was obtained for the calcium citrate composition of the present invention. A preferred density range is between about 2.2 g/cc and about 2.6 g/cc. A corresponding density value of about 2.0 g/cc was obtained for Pfizer calcium citrate tetrahydrate.

Surface area measurments of the calcium citrate composition of the present invention and commercial calcium citrate tetrahydrate were conducted. The standard B.E.T. procedure of Brunauer et alia (J. Am. Chem. Soc. 59, 2682 (1937) and J. Am. Chem. Soc. 60, 309 (1938)) was used for these surface area measurments. The commercial calcium citrate tetrahydrate had a surface area of about 10 $m^2$/g and the calcium citrate composition of the present invention had a surface area of about 1/10 this value.

The dried calcium citrate composition was subjoined with 1.5 weight percent magnesium stearate and 1 weight percent cellulose gum and passed through a Fitzmill model no. 6 communator (Fitzpatrick) with a 3162AA screen and blended for about 5 minutes to form a tableting composition. The screen size preferred is one which permits the production of particles large enough to flow yet small enough to prevent packing.

The tableting composition was then tableted in a multiple station tablet press to form calcium citrate tablets comprising at least about 150 mg calcium. Multiple station tablet presses such as a Cotton #216-16 station press; a Vector #247-41 station press; or a Manesty rotopress-37 station press, for example may be used. The tablets thus obtained may be final products or may be further processed.

Further processing to physically and aesthetically improve these tablets may be accomplished by tablet coating procedures well known to those skilled in relevant pharmaceutical arts. For example, a coating comprising polyvinylpyrrolidone (PVP), sugar, water, calcium-carbonate and titanium dioxide was placed on tablets comprising 200 mg calcium. This coating procedure was by conventional pharmaceutical pan-coating technology.

Calcium carbonate (300 moles) was thoroughly mixed with 200 moles citric acid (anhydrous or hydrated citric acid are both usable). This mixing may be accomplished in a well-known variety of manners. It has been found that a quantity of heated water (50° C.–80° C.) between 30 kg and 60 kg, preferably between about 40 kg and about 50 kg should be gradually added (more rapidly of first) with continuous mixing until the mass of material attains a granular consistency. This material may then be dried, for example at a temperature between about 60° C. and about 80° C., until the moisture content is between about 10 weight percent and about 13 weight percent. These variations arm meant to summarize the results of many months of experimentation in this area and to elucidate workable variations in the preferred embodiment presented in the immediately preceding example.

The procedures of the immediate preceding example were followed but the amount of citric acid was increased 120% to 300%. The resultant calcium citrate–citric acid composition was dried to a moisture content of less than about 2 weight percent and found to be suitable for tableting.

Calcium citrate (1 mole) and citric acid (1 mole) were blended and then mixed with water (10 mole at 60° C.). After thorough blending the mixture was dried at 170° F. for 2 days. The dried composition had a bulk density of about 0.85 g/cc. The dried composition was mixed with 4 weight percent microcrystalline cellulose (FMC Corp., Newark, Del. 19711), 1 weight percent magnesium stearate and 1 weight percent cellulose gum to produce a tableting composition.

The tableting composition was then processed through a conventional multistation tableting press to produce tablets having a calcium/(citrate-citric acid) molar ratio of 1/1. Properties of these 1/1 calcium citrate tablets are shown in the following table:

Calcium/Citrate 1/1 Tablets
0.71 cc/tablet
1.39 g/cc
990 mg/tablet
211 mg Ca/cc
150 mg Ca/tablet
15.2 wt % Ca
1/1 Cacitrate/citric acid molar ratio
16.1 mm length
10.5 mm width

DETAILED DESCRIPTION OF THE PREFERRED EMBODIMENTS

The present invention provides a vitamin and mineral supplement containing calcium citrate and carbonyl iron. Supplements of the present invention may be used as a dietary supplement by a man, woman, or a child by adjusting the levels of ingredients to the recommended dietary allowance for those categories of individuals (according to the Food and Nutrition Board, National Academy of Sciences-National Research Council, 1989, in: Remington: The Science and Practice of Pharmacy, Gennaro, Ark., ed., 1995, Mack Publ Co., Easton Pa., p. 1108, incorporated by reference herein). In particular, a supplement as provided herein is for pregnant or lactating women, or for women of reproductive years who may become pregnant. Although not limited thereto, a preferred embodiment of the supplement is for pregnant or lactating women and has the tradename PRENATE® ULTRA™.

ULTRADENSE™ Calcium Citrate

ULTRADENSE™ calcium citrate is described in U.S. Pat. Nos. 4,814,177; 4,851,221; and 4,772,467; each patent is incorporated herein by reference in its entirety. Calcium citrate is a superior vehicle for dietary calcium supplementation as compared to calcium carbonate, the more commonly used source of calcium. The ingestion of calcium citrate in a usual form having a density of 0.7 g/cc presents a problem in that the bulkiness of usual calcium citrate makes incorporating adequate amounts of calcium in a desired tablet size difficult. U.S. Pat. No. 4,814,177, previously incorporated by reference herein, provides a method for making exceedingly dense calcium citrate tablets.

The bulk density of ULTRADENSE™ calcium citrate used in the present invention is between about 0.9 g/cc and 1.3 g/cc, preferably between about 1.0–1.2 g/cc, and more preferably between about 1.0–1.1 g/cc. This high density and the fact that calcium is 21% of the weight of ULTRADENSE™ calcium citrate allows a high amount of calcium to be included in a supplement tablet where carbonyl iron and the recommended dietary allowance of a number of vitamins and minerals can also be provided; nevertheless, the total weight of the tablet is only about 1.5–1.6 g.

Unlike calcium carbonate and other calcium salts commonly found in dietary supplements, calcium citrate does not rely on stomach acid to dissolve. Calcium citrate is soluble in both stomach acid and in the more alkaline environment of the small intestine. Consequently, stomach acid is more available for solubilizing other minerals, such as iron, for example. Further, in clinical testing, calcium citrate has been shown to be more soluble, better absorbed, and better tolerated than traditional calcium supplements such as calcium carbonate. A method of making calcium citrate as used herein is provided in Example 1. calcium citrate is present in the formulation in an amount to provide from about 100–300 mg calcium, preferably, 150–250 mg calcium, and more preferably, about 200 mg calcium in a single dosage form.

Supplemental calcium is especially beneficial for the skeletal system, for humans intolerant of lactose, for pregnant and lactating women where fetal demands require substantial amounts of calcium and for post-menopausal women.

Carbonyl Iron

In comparing carbonyl iron to the iron (ferrous) salts (ferrous sulfate, ferrous fumarate, ferrous gluconate and others), the elemental iron forms have a 96–98% iron content while ferrous salts have only a 12–32% iron content. Therefore, in order to provide 1 mg of iron in a supplement, it is necessary to use 3 mg (or more) of a ferrous salt compared to 1 mg of elemental iron, provided that both forms have similar absorption rates. Consequently, significant tablet space is saved using elemental iron rather than an iron salt. Carbonyl iron can be obtained from International Specialty Products (Wayne, N.J.) or BASF (Mount Olive, N.J.), for example. Carbonyl iron is preferably present in the formulation in an amount to provide from about 30–120 mg iron, more preferably 60–120 mg iron, and most preferably, about 90 mg iron in a single dosage form.

The vitamins and minerals described below are of food-grade approved for use in humans (see, U.S. Pharmacopeia, 23rd edition, U.S. Pharmacopeia Inc.); they may be obtained from common distributors known to one of skill in the art in light of this disclosure, such as, for example; Hoffman-LaRoche, Inc., (Nutley, N.J.); BASF (Mount Olive, N.J.); Takeda (Orangeburg, N.Y.); Mallinckrodt (Chesterfield, Mo.); or Spectrum (Gardena, Calif.), for example.

Vitamin A and Beta Carotene

Beta carotene and Vitamin A (retinol) provide the total Vitamin A in the present formulation in amounts of about 2000–4000 I.U., more preferably about 2200–2300 I.U., and most preferably about 2700 I.U. Use of beta carotene to provide a portion of the total Vitamin A reduces risk of toxicity from preformed vitamin A. A pharmaceutically acceptable salt of vitamin A can be used, exemplary salts are acetate and palmitate, for example.

B Vitamins

B vitamins of the present composition include vitamin B1 (thiamine) in a single dosage amount from about 1.0–5.0 mg, more preferably 2.0–4.0 mg, and most preferably about 3 mg; vitamin B2 (riboflavin) in an amount from about 1.0–5.0 mg, more preferably 2.0–4.0 mg, and most preferably about 3 mg; vitamin B6 (pyridoxine, pyridoxal, pyridoxamine) in an amount from about 1.0–25 mg, more preferably 10–25 mg, and most preferably about 20 mg; vitamin B12 (cyanocobalamin) in an amount from about 2.0–12 mcg, preferably 6–12 mcg, and most preferably about 12 mcg; niacin or nicotinic acid or niacinamide in an amount from about 10–30 mg, preferably 15–25 mg, and most preferably about 20 mg; and folic acid in an amount from about 0.2–2.4 mg, preferably 0.4–1.5 mg, and most preferably about 1 mg. Pharmaceutically acceptable forms of certain of the B vitamins include, but are not limited to, thiamine mononitrate or thiamine hydrochloride; niacin or niacinamide; and pyridoxine hydrochloride.

Vitamin C

Vitamin C is present as ascorbic acid, or may be present as dehydroascorbic acid in an amount from about 30–300 mg, more preferably 60–200 mg, most preferably about 120 mg. Pharmaceutically acceptable salts include, but are not limited to, sodium or calcium ascorbate.

Vitamin D

Vitamin D used in the present supplement can include any of the forms of vitamin D that is a precursor to 1,25-dihydroxycholecalciferol. Vitamin D is preferably present in a supplement of the present invention in an amount from about 200–600 I.U., more preferably 300–500 I.U., and most preferably about 400 I.U. Vitamin D3 (cholecalciferol) or D2 (ergocalciferol) is preferred.

Vitamin E

Vitamin E can be present as $\alpha$-, $\beta$-, $\gamma$-, or $\delta$-tocopherol or as a mixture, or as an isomer thereof, such as D-$\alpha$-tocopherol acetate or DL-$\alpha$-tocopherol acetate. Salts of vitamin E include, but are not limited to, an acetate, or acid succinate salt. Vitamin E is preferably present in a supplement of the present invention of from about 30–400 I.U., preferably 30–100 I.U. and more preferably about 30 I.U. (1 I.U. approximately equals 1 mg).

Iodine

Iodine can be present as a potassium salt, and is preferably present in an amount of about 100–300 mcg, more preferably, of about 120–220 mcg, and most preferably about 150 mcg.

Copper

Copper may be present as a sulfate, nitrate, chloride, carbonate, oxide, hydroxide, iodide, glutamate, glycerophosphate, aspartate, citrate, nucleinate, pyrophosphate, or the like. The amount of copper is preferably from about 1.5–3.0 mg, more preferably about 2.0–2.5 mg, and most preferably about 2.5 mg.

Zinc

Zinc can be provided from a wide variety of inorganic salts such as oxide, phosphate, chloride, sulfate, nitrate, gluconate, or the like; as well as from metallic zinc in amounts from about 10–60 mg, more preferably from about 15–40 mg, most preferably about 25–35 mg.

Further vitamins or minerals including but not limited to vitamin K, phosphorous, magnesium, selenium, biotin, choline, inositol, pantothenic acid, chromium, cobalt, fluorine, manganese, nickel, or the like, may be added to the supplements of the present invention and still be within the scope of the claims.

Further Advantages

The present formulation preferably contains a laxative such as docusate sodium in an amount ranging from about 25–75 mg, preferably an amount of about 40–60 mg, and most preferably an amount of about 50 mg/tablet. Docusate sodium can be obtained from Ceres Chem. Co. (Harrison, N.Y.). Other forms may include docusate calcium.

The present formulation is thought to be hypoallergenic in that none of the components are known to have a history of allergy activity, and the formulation has Kosher certification by inspection and citation that the materials and processes used are Kosher.

Disintegrating agents may be included in the present formulation to assist in the dissolution of the tablet in the stomach. Disintegrating agents are well known in the art in light of this disclosure, and include, but are not limited to, starch, or carboxymethylcellulose, for example. A preferred disintegrating agent is croscarmellose sodium.

Lubricating agents may be included in the present formulation to assist in compression of the formulation so that a tablet does not stick in a tablet press. Lubricants are well known in the art in light of this disclosure, and include, but are not limited to, stearic acid, talc, calcium stearate, zinc stearate, magnesium stearate, or the like. A preferred lubricant is magnesium stearate.

The present supplement may include an aroma enhancer, such as ethyl vanillin, for example, to provide a pleasant aroma. Ethyl vanillin, in particular, is able to mask the characteristic smell associated with B complex vitamins. The ethyl vanillin aroma, therefore, provides patient satisfaction and acceptability.

The small size of the tablet is an advantage, since small size increases patient acceptability in that the tablet is easier to swallow. The small size is accomplished in a number of ways: use of ULTRADENSE™ calcium citrate which provides calcium in a more dense form than other calcium citrate preparations, use of carbonyl iron which takes up less tablet space than an iron salt, use of a granulating agent such as ethyl cellulose to form an ULTRADENSE™ calcium citrate granular form, use of a granulating agent such as povidone to form other ingredients as indicated in Example 1 into a granular form, and blending of the two granular forms to form a blend. These compositions and procedures allow a tablet of about 1.5–1.6 g to be made. Bulk density of a composition and tablet density may be measured by procedures as described in U.S. Pat. No. 4,814,177, incorporated by reference herein for these purposes.

Many other pharmaceutically acceptable tableting binders, lubricants, disintegrants, carriers and excipients known in the pharmaceutical arts in light of the present disclosure are usable in the production of tablets of the present invention (See, e.g., Remington: The Science and Practice of Pharmacy, Gennaro, Ark., ed., 1995, Mack Publ. Co., Easton Pa., p. 1615, incorporated by reference herein). As used herein, pharmaceutically acceptable is a component that is suitable for use in humans without undue side effects, such as irritation, toxicity, or allergic response.

The tableting composition is fed through a multiple station D-tool tablet press to form tablets. Multiple station tablet presses such as a Manesty Mark 345 station press, a Fette 45 station press, or a Manesty rotopress-37 station press, for example, may be used, but are not limited thereto.

Further processing to physically and aesthetically improve the tablets may be accomplished by tablet coating procedures well known to those skilled in relevant pharmaceutical arts. For example, the solid dosage form may have a film coating to protect the ingredients from moisture, oxygen, or light; or to mask any undesirable taste or appearance. Suitable coating agents include cellulose, hydroxypropylmethylcellulose, cellulose phthalate, methacryulic copolymer, polyvinylpyrrolidone (PVP), sugar, titanium dioxide, or shellac. An enteric coating may be employed, as well as coloring agents for identification, and if desired, the solid form may be polished with a waxy composition, such as carnauba wax. Coating procedures are by conventional pharmaceutical pan-coating technology known by those of skill in this art in light of this disclosure.

The present supplement may be provided in oral solid dosage form for example, a tablet, capsule, lozenger, chewable tablet or bulk powder.

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Preparation of a Vitamin and Mineral Supplement Containing ULTRADENSE™ Calcium Citrate and Carbonyl Iron The present example provides a particular embodiment of the supplement composition of the present invention, and a method of making the composition. Table 1 provides a preferred single dose and bulk formulation.

TABLE 1

A Vitamin and Mineral Supplement Containing ULTRADENSE ™ Calcium Citrate and Carbonyl Iron

| (mg/Tablet) | Ingredient | Overage %[a] | kg | gm | mg |
|---|---|---|---|---|---|
| 90 | Elemental Iron (carbonyl iron, powder) | | 72 | 0.00 | |
| 0.2 (0.15 as iodine) | Iodine (potassium iodide powder) | 40 | | 224 | |
| 970 (200 as elemental calcium) | Calcium (ULTRADENSE ™ calcium citrate, 98%) | | 776 | 0.00 | |
| 2.5 | Copper (cupric oxide) | | 2 | 0.00 | |
| 31.12 | Zinc (zinc oxide) | 2 | 25 | 394 | |
| 1.0 | Folic Acid | 35 | 1 | 080 | |
| 6.8 | Vitamin A palmitate, 250,000 I.U./g (1700 I.U./Tablet) | 30 | 7 | 072 | |
| 5.99 | β-carotene, 10%, 0.167 × 10$^6$ I.U./g (1000 I.U./Tablet), (a total of 2700 I.U. Vit A + β-carotene) | 40 | 6 | 709 | |
| 4.0 | Vitamin D3 (cholecalciferol), 100,000 I.U./g (400 I.U./T) | 40 | 4 | 480 | |
| 60 | Vitamin E (dl-α tocopherol acetate), 50%, (30 I.U./T) | 10 | 52 | 800 | |
| 123.7 | Vitamin C (ascorbic acid), 97% | 10 | 108 | 866 | |

TABLE 1-continued

A Vitamin and Mineral Supplement Containing
ULTRADENSE ™ Calcium Citrate and Carbonyl Iron

| (mg/Tablet) | Ingredient | Overage %[a] | kg | gm | mg |
|---|---|---|---|---|---|
| 3.26 | Vitamin B1 (thiamine mononitrate) | 25 | 3 | 260 | |
| 3.4 | Vitamin B2 (riboflavin) | 20 | 3 | 264 | |
| 24.3 | Vitamin B6 (pyridoxine HCl) | 20 | 23 | 328 | |
| 0.012 | Vitamin B12 (cyanocobalamin, crystalline, 100%) | 40 | | 13 | 440 |
| 20 | Niacinamide | 20 | 19 | 200 | |
| 58.82 | Docusate Sodium (85%) | | 47 | 056 | |
| 37.5 | Povidone | | 30 | 0.00 | |
| 30 | Croscarmellose Sodium | | 24 | 0.00 | |
| 15 | Magnesium Stearate | | 12 | 0.00 | |
| 2.0 | Ethyl Vanillin | | 1 | 600 | |
| Total weight/Tablet: 1525.42 mg | | | Total weight 1220.346 kg | | |

[a] the excess amount of an ingredient used to assure potency prior to an expiration date.

ULTRADENSE™ calcium citrate was made according to methods provided in U.S. Pat. No. 4,814,177, incorporated by reference herein for this specific purpose. Stoichiometric amounts of calcium carbonate, citric acid, and water were mixed together to produce calcium citrate and carbon dioxide. In a second phase of the reaction, the gray slurry turned white and shrunk to about 50% of its volume. This ULTRADENSE™ material was nearly dry and had a density of about 1.1–1.2 g/cc; the water had become water of crystallization. Alcoholic ethyl cellulose was added at the time of solidification in a 2:98 ratio of ethyl cellulose to ULTRADENSE™ calcium citrate for granulation to form a first granular mixture. Granulation assists in the compressibility of tablets. Separately, Vitamin E, docusate Na, zinc oxide, copper oxide, and one-half of the carbonyl iron was granulated with povidone, a polymeric granulation agent to form a second mixture. The two mixtures are blended in a blender, the rest of the ingredients are added and blended further. The bulk mixture is then ready for compression into tablets. The bulk density of this blend is about 0.9 to 1.1 g/cc. No other formulation having the amounts of ingredients provided herein and having the cited density is known.

An important aspect of the vitamin and mineral formulation of the present invention is the elegance of the small-sized tablet. If the calcium citrate was not ULTRADENSE™ calcium citrate and if carbonyl iron was not used, the resultant tablet would be prohibitively large. Therefore, use of ULTRADENSE™ calcium citrate and use of carbonyl iron contribute to making the present formulation compressible into acceptably-sized tablets. The weight of tablets of the present formulation is between about 1.5 and 1.6 grams. The surface area is about 0.869 square inches, and the volume is about 0.0599 cubic inches.

EXAMPLE 2

In Vitro Solution Properties of ULTRADENSE™ Calcium Citrate, Carbonyl Iron, and Zinc Studies were performed to examine the in vitro solution properties of calcium and iron under conditions where the calcium is present as calcium carbonate or calcium citrate, and the iron is present as carbonyl iron.

Iron dissolution study #1
SAMPLE: Elemental iron, specially processed to a 3.5 micron size, 60 mg.
DISSOLUTION MEDIUM: Water, 300 mL, 37° C., 1 hour test, USP paddle method.
PURPOSE: To study the effect of vitamin C on the dissolution of iron in water.

| mg Vitamin C | % Fe | Precipitation in alkaline bicarbonate |
|---|---|---|
| 0 | 0 | — |
| 50 | 2.43 | None |
| 150 | 13.92 | None |
| 250 | 31.04 | None |
| 500 | 42.74 | None |

The data demonstrate that iron is increasingly soluble with increasing amounts of ascorbate present in a solution. Upon adding bicarbonate, there was no precipitation of iron.

Iron dissolution study #2
SAMPLE: Elemental iron, specially processed to a 3.5 micron size, 60 mg.
DISSOLUTION MEDIUM: 0.08 N hydrochloric acid, 300 mL, 37° C., 1 hour test, USP paddle method.
PURPOSE: To study the effect of vitamin C on the dissolution of iron in gastric acid.

| mg Vitamin C | % Fe | Precipitation in alkaline bicarbonate | % Fe remaining in solution |
|---|---|---|---|
| 0 | 84.90 | YES | 0.0 |
| 250 | 98.31 | NO | 98.31 |
| 500 | 98.40 | NO | 98.40 |

The data demonstrate that iron is more soluble in dilute acid than in water, and that the iron precipitates out upon addition of bicarbonate when ascorbate is not present.

Iron dissolution study #3
SAMPLE: Elemental iron, specially processed to a 3.5 micron size, 60 mg.
DISSOLUTION MEDIUM: Water or 0.08 N hydrochloric acid, 300 mL, 37° C., 1 hour test, USP paddle method.
PURPOSE: To study the effect of calcium carbonate on the dissolution of iron in gastrointestinal media in the presence of vitamin C.

| mg Vitamin C | mg $CaCO_3$ | % Fe | precipitation | % Fe |
|---|---|---|---|---|
| 250 | 400 | 89.42 | YES | 36.72 |
| 500 | 400 | 96.1 | YES | 59.96 |

The data demonstrate that even in the presence of ascorbate, when calcium is in the form of calcium carbonate, iron precipitates out of solution.

Iron dissolution study #4
SAMPLE: Elemental iron, specially processed to a 3.5 micron size, 60 mg.
DISSOLUTION MEDIUM: 0.08 N hydrochloric acid, 300 mL, 37° C., 1 hour test, USP paddle method.
PURPOSE: To study the effect of calcium citrate on the dissolution of iron in gastrointestinal fluids in the presence of vitamin C.

| mg Vitamin C | mg Calcium Citrate | % Fe | precipitation | % Fe |
|---|---|---|---|---|
| 250 | 750 | 98.0 | None | 98.0 |
| 500 | 750 | 98.0 | None | 98.0 |

These data demonstrate that iron is soluble when calcium is in the form of citrate. These results are contrasted to those of study #3 where calcium was present in the form of calcium carbonate and the iron precipitated out.

In dilute HCl, such as in the stomach, calcium from calcium carbonate dissolves; however, under alkaline conditions, such as in the small intestine, calcium carbonate precipitates and traps iron in the process of precipitating. Therefore, iron is not as available for absorption when calcium is provided as calcium carbonate.

In contrast, calcium citrate is soluble both under stomach acid conditions and under the more alkaline conditions found in the small intestine. Therefore, iron is more available for absorption when calcium is provided as calcium citrate.

Zinc is more soluble in the presence of vitamin C since it forms zinc ascorbate, and is then more available for absorption. In the presence of calcium carbonate and vitamin C, calcium will form calcium ascorbate, thereby tying up the ascorbate and making it less available for solubilizing zinc. In contrast, calcium citrate in the presence of vitamin C does not form calcium ascorbate, and ascorbate is free to solubilize zinc. Therefore, by having calcium present in the form of citrate, both iron and zinc are more available for absorption.

EXAMPLE 3

In Vivo Absorption of Zinc, Calcium, and Magnesium as a Result of PRENATE 90® vs. PRENATE® ULTRA™ Supplementation The present example provides the results of in vivo studies on the uptake of zinc, calcium, and magnesium from PRENATE® 90 vs. PRENATE® ULTRA™ vitamin and mineral supplements. PRENATE® 90 is a prenatal formulation marketed by Bock Pharmacal Co. (St. Louis, Mo.). Table 2 provides the compositions of each supplement for comparison.

TABLE 2

Comparison of the Amounts and Sources of Ingredients for Supplements Used in In Vivo Tests

| Ingredient | PRENATE® ULTRA™ (mg/Tablet) | PRENATE® 90 (mg/Tablet) |
|---|---|---|
| Elemental Iron | 90, (carbonyl iron) | 90, as ferrous fumarate |
| Iodine | 0.2 | 0.15 |
| Calcium | 200, (ULTRADENSE™ calcium citrate) | 250, as calcium carbonate |
| Copper | 2.5 | 2 |
| Zinc | 31.12 | 25 |
| Folic Acid | 1.0 | 1 |
| Vitamin A | 6.8, as palmitate, 250,000 I.U./g (1700 I.U./T); and β-carotene, 10%, 5.99 mg, 0.167 × $10^6$ I.U./g (1000 I.U./T) | 1.2, as acetate (4000 I.U.) |
| Vitamin D3 | 4.0, 100,000 I.U./g (400 I.U./T) | .01, (400 I.U.) |
| Vitamin E | 60, (50%) (30 I.U.) | 30, (30 I.U.) |

TABLE 2-continued

Comparison of the Amounts and Sources of Ingredients for Supplements Used in In Vivo Tests

| Ingredient | PRENATE® ULTRA™ (mg/Tablet) | PRENATE® 90 (mg/Tablet) |
|---|---|---|
| Vitamin C | 123.7, (97%) | 120 |
| Vitamin B1 | 3.26 | 3 |
| Vitamin B2 | 3.4 | 3.4 |
| Vitamin B6 | 24.3 | 20 |
| Vitamin B12 | 0.012 | 0.012 |
| Niacinamide | 20 | 20 |

Methods

The uptake of zinc, calcium and magnesium was determined by analyzing urine for those minerals over a 7-h collection period from volunteers who took the cited supplements.

The study was conducted with nine healthy female volunteers ranging from 25–45 years of age (mean 36.8 years). Informed consent was obtained from all subjects and none of the women were pregnant.

The subjects were instructed to discontinue use of any vitamins or mineral supplements two days prior to the beginning of the study. During the study, all volunteers were instructed to ingest a diet void of citrate; thus avoiding fruits, tomatoes and fruit juices. They were further instructed during the 2-day collection period to eat very similar meals (lunch and dinner) to prevent dietary influences. Their fluid intake was fixed at 2.5–3.0 L per day of deionized water.

The evening before collection day, subjects were instructed to fast after 7 P.M. with only deionized water intake. On the morning of the collection period, the subjects were in a fasting state when they ingested 3 tablets of either the PRENATE® 90 or PRENATE® ULTRA™ supplement, chosen in a randomized order. After tablet ingestion, the subjects collected urine for a period of 7 h. On the next day, subjects ingested 3 tablets of the other supplement and urine was collected as on the first day. A morning baseline was collected to assure no carryover of supplement from the previous day's test.

Urine was analyzed for total volume, zinc, calcium, magnesium, and creatinine. Zinc, calcium and magnesium were analyzed by atomic absorption spectrometry and creatinine by a kinetic modification of the Jaffe method (Larsen, K., *Clin. Chem. Acta.* 41:209–217, 1972). Zinc, calcium, and magnesium were standardized to the amount of creatinine excreted to avoid any problems with the urine collections.

Statistical analyses were performed comparing the sample means of the two day collection periods using the student t-test. This analysis was performed using QUATTROPRO® statistical software (Novell Inc., Orem, Utah). Data are expressed as the mean plus or minus standard deviation.

Results

Zinc is absorbed from both supplements, however, there is a statistically significant increase in urinary zinc with the PRENATE® ULTRA™ supplement compared to that of PRENATE® 90 as shown in FIG. 1. Therefore, the PRENATE® ULTRA™ supplement provides for better absorption of zinc as compared to the PRENATE® 90 supplement.

Figure 2:
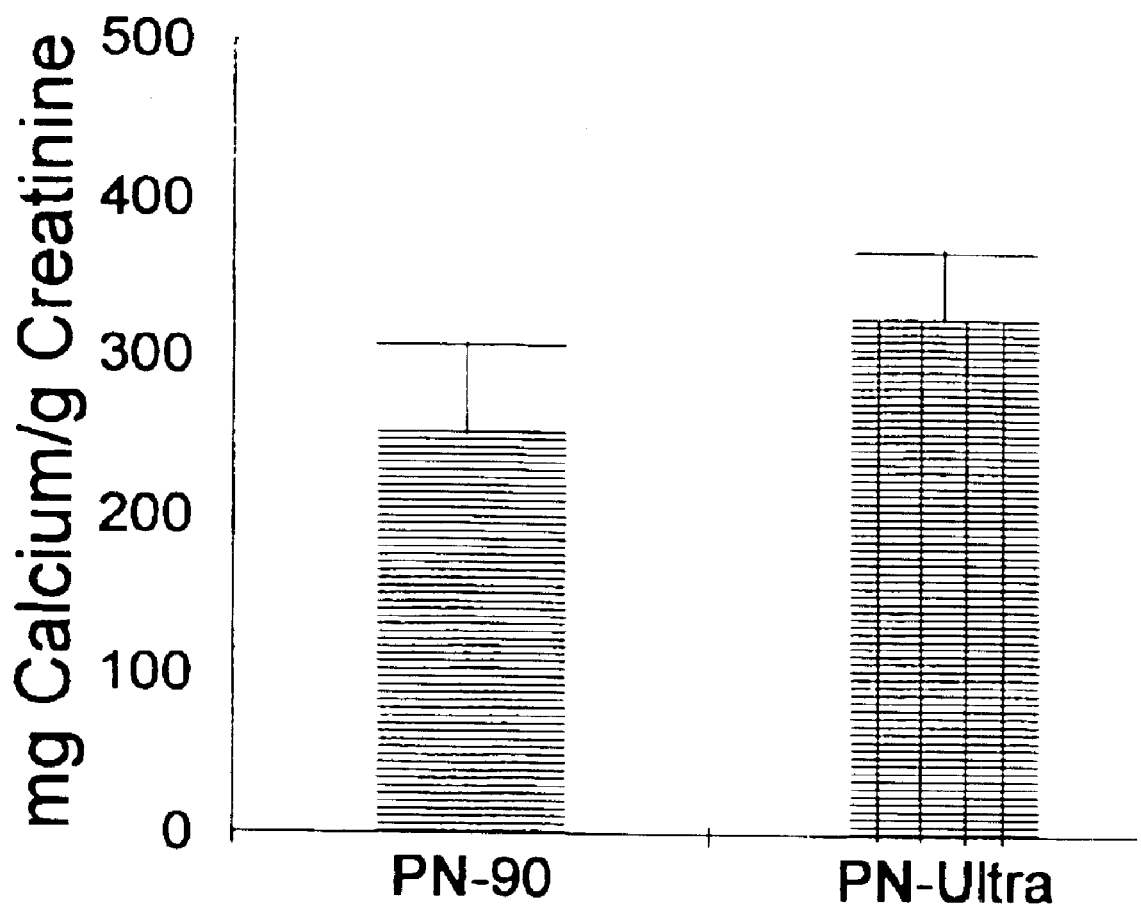
FIG. 2 provides a standard error analysis of data obtained from urine samples analyzed for calcium content after oral ingestion of either PRENATE® ULTRA™ (PN-Ultra) or PRENATE® 90 (PN-90). A difference of $p<0.07$ was found between the means of the two different supplements. Error bars represent standard error, n=9. See Example 3 for methods.

Calcium is demonstrated to be more bioavailable in the PRENATE® ULTRA™ supplement compared to the bioavailability from the PRENATE® 90 supplement (FIG. 2). These data provide further evidence that calcium in the citrate form is more soluble than calcium in the carbonate form.

Figure 3:
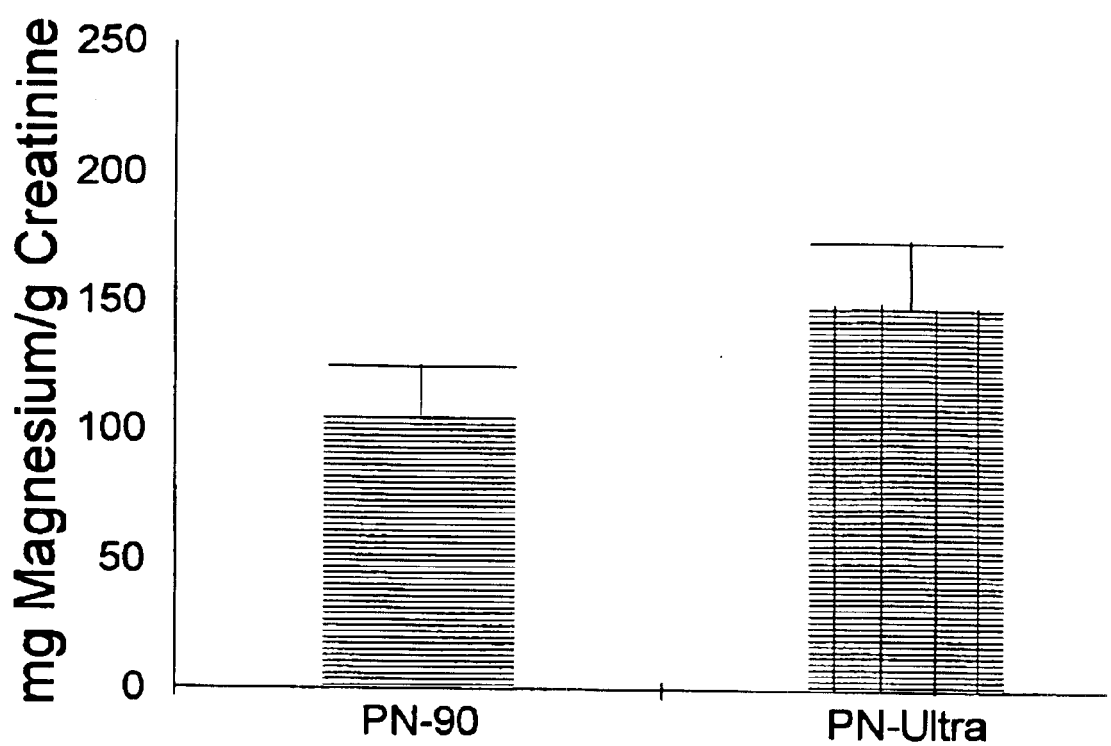
FIG. 3 provides a standard error analysis of data obtained from urine samples analyzed for magnesium content after oral ingestion of either PRENATE® ULTRA™ (PN-Ultra) or PRENATE®90 (PN-90). A significant difference of $p<0.03$ was found between the means of the two different supplements. Error bars represent standard error, n=9. See Example 3 for methods.

Magnesium is difficult to provide as a supplement since it causes a strong saline cathartic effect, i.e., it causes diarrhea. Magnesium is not a constituent of either supplement of the present study in significant amounts, however, the results show a statistically significant increase in magnesium absorption from dietary magnesium with the PRENATE® ULTRA™ supplement when compared to the PRENATE® 90 supplement (FIG. 3). Therefore, the PRENATE®ULTRA™ supplement appears to enhance bioavailability of magnesium ingested from a normal diet. This enhanced uptake is especially significant for obstetrical patients, since magnesium sulfate in bolus form has long been used for preventing premature labor.

Not wanting to be bound by theory, the present inventors expect that the present formulation would enhance uptake of further divalent cations since ascorbate and citrate may facilitate complex formation with divalent cations and stimulate both active and passive transport for in vivo absorption.

EXAMPLE 4

In Vivo Absorption of Iron as a Result of PRENATE 90® vs. PRENATE® ULTRA™ Supplementation Uptake of iron from the prenatal supplements cited in Example 3 will be measured in serum, 3 hours after ingestion, in a fasting state. This study will be conducted with 10–15 healthy female volunteers of childbearing age (up to 45 years old). Informed consent will be obtained from all subjects and none of the women will be pregnant.

The subjects will be instructed to discontinue use of any vitamins or mineral supplements three days prior to the beginning of the study. The day prior to the ingestion of the prenatal supplement tablets, all volunteers will be instructed to ingest a diet void of red meats and citrate (thus avoiding fruits, tomatoes and fruit juices). The evening before the collection day, subjects will be instructed to fast after 7 P.M. with only deionized water intake. The following morning, subjects will be given 3 tablets of either the PRENATE® ULTRA™ supplement or PRENATE®90, chosen in a randomized order. Subjects will remain in a fasting state until their blood is drawn, 3 hours post-supplement ingestion. On the next day, subjects will ingest 3 tablets of the other supplement and blood will be collected as on the first day. A morning baseline will be collected to assure no carryover of supplement from the previous day's test.

Venous blood samples will be drawn by vacutainer and allowed to clot at room temperature; serum will be separated from whole blood by centrifugation. Serum will be removed and stored at −20° C. until analyzed. Hemolyzed specimens will not be analyzed. The samples will be analyzed for total iron by spectrophotometry using a Ferene chromogen, Roche Diagnostics (Hoffman-LaRoche, Inc., Nutley, N.J.).

Statistical analysis will be performed comparing the sample means of the two different collection periods using the student t-test. This analysis will be performed using QuattroPro statistical software as cited in Example 3. Data are expressed as the mean plus or minus standard deviation.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A single-dose dietary supplement comprising:

calcium citrate, wherein the calcium citrate provides from about 100 mg to about 300 mg calcium; and carbonyl iron, wherein the carbonyl iron provides from about 60 mg to about 120 mg iron;

the calcium citrate having a bulk density of between 0.9 g/cc and 1.3 g/cc.

2. The supplement of claim 1 wherein the single dose is a tablet weighing less than about 1.6 g.

3. A single-dose dietary supplement comprising:

calcium citrate having a bulk density of between 0.9 g/cc and 1.3 g/cc, wherein the calcium citrate provides from about 100 mg to about 300 mg calcium; carbonyl iron, wherein the carbonyl iron provides from about 60 mg to about 120 mg iron; and a vitamin.

4. A single-dose dietary supplement comprising calcium citrate having a bulk density of between 0.9 g/cc and 1.3 g/cc, wherein the calcium citrate provides from about 100 mg to about 300 mg calcium; carbonyl iron, wherein the carbonyl iron provides from about 60 mg to about 120 mg iron; and at least one vitamin selected from the group consisting of vitamin A, vitamin B1, vitamin B2, vitamin B6, vitamin B12, vitamin C, vitamin D, vitamin E, folic acid, iodine, copper, zinc, niacinamide, and any combination thereof.

5. The supplement of claim 4 wherein, vitamin A is present in an amount from about 2000–4000 I.U.;

vitamin B1 is present in an amount from about 1.0–5.0 mg;

vitamin B2 is present in an amount from about 1.0–5.0 mg;

vitamin B6 is present in an amount from about 1.0–25.0 mg;

vitamin B12 is present in an amount from about 2–12 mcg;

vitamin C is present in an amount from about 30–300 mg;

vitamin D is present in an amount from about 200–600 I.U.;

vitamin E is present in an amount from about 30–400 I.U.;

folic acid is present in an amount from about 0.2–2.4 mg;

iodine is present in an amount from about 100–300 mcg;

copper is present in an amount from about 1.5–3.0 mg;

zinc is present in an amount from about 10–60 mg; and niacinamide is present in an amount from about 10–30 mg.

6. Previously Presented) The supplement of claim 4 wherein the calcium citrate is present in an amount to provide about 200 mg calcium;

carbonyl iron is present in an amount to provide about 90 mg iron;

vitamin A is present in an amount of about 2700 I.U.;

vitamin B1 is present in an amount of about 3 mg;

vitamin B2 is present in an amount of about 3.4 mg;

vitamin B6 is present in an amount of about 20 mg;

vitamin B12 is present in an amount of about 12 mcg;

vitamin C is present in an amount of about 120 mg;

vitamin D is present in an amount of about 400 I.U.;

vitamin E is present in an amount of about 30 I.U.;

folic acid is present in an amount of about 1 mg;

iodine is present in an amount of about 150 mcg;

copper is present in an amount of about 2 mg;

zinc is present in an amount of about 25 mg; and niacinamide is present in an amount of about 20 mg.

7. A vitamin and mineral dietary supplement made by a process comprising the steps of:

granulating calcium citrate having a bulk density of between 0.9 g/cc and 1.3 g/cc with a first granulating agent to form a first granular mixture;

granulating Vitamin E, docusate Na, zinc, copper, and carbonyl iron with a second granulating agent to form a second granular mixture;

blending the first mixture with the second mixture to form a first blend;

adding to the first blend an ingredient selected from the group consisting of carbonyl iron, vitamin A, vitamin B1, vitamin B2, vitamin B6, vitamin B12, vitamin C, vitamin D, folic acid, iodine, niacinamide, and any combination thereof to the first blend; and blending the first blend and added ingredient to form a second blend, wherein the second blend is the vitamin and mineral dietary supplement.

8. The supplement of claim 7 wherein the first granulating agent is ethyl cellulose.

9. The supplement of claim 8 wherein the ethyl cellulose is present in a ratio to calcium citrate of about 2:98.

10. The supplement of claim 7 wherein the second granulating agent is povidone.

11. The supplement of claim 7 wherein the second blend has a bulk density of between 0.9 g/cc and 1.1 g/cc.

12. A method of making a vitamin and mineral dietary supplement comprising the steps of granulating calcium citrate having a bulk density of between 0.9 g/cc and 1.3 g/cc with a first granulating agent to form a first granular mixture;

granulating Vitamin E, docusate Na, zinc, copper, and carbonyl iron with a second granulating agent to form a second granular mixture;

blending the first mixture with the second mixture to form a first blend;

adding to the first blend an ingredient selected from the group consisting of carbonyl iron, vitamin A, vitamin B 1, vitamin B2, vitamin B6, vitamin B12, vitamin C, vitamin D, folic acid, iodine, niacinamide, and any combination thereof to the first blend;

blending the first blend and added ingredient to form a second blend; and formulating the second blend into an oral dosage form.

13. The method of claim 12 wherein the second blend has a bulk density of between 0.9 g/cc and 11.1 g/cc.

14. A method of treating a vitamin or mineral deficiency of a human, the method comprising themes step of:

administering the supplement of claim 4 the human having a vitamin or mineral deficiency.

15. The method of claim 14 wherein the human is pregnant or lactating.

16. The method of claim 14 wherein the human is a blood donor.

17. The method of claim 14 wherein the human is anemic.

18. A method of treating a deficiency of calcium or iron in a human, the method comprising the step of:

administering the supplement of claim 4 to the human having a deficiency of calcium or iron.

19. A method of enhancing uptake of magnesium from a diet of a human in need of enhanced uptake of magnesium, comprising the step of:

administering the supplement of claim 4 to the human wherein uptake of magnesium is enhanced when compared to uptake of magnesium in the absence of the supplement.

20. The supplement of claim 4 further comprising vitamin A, vitamin B1, vitamin B2, vitamin B6, vitamin B 12, vitamin C, vitamin D, vitamin E, folic acid, iodine, zinc, and niacinamide are provided in at least the recommended daily allowance for pregnant or lactating women.

21. The supplement of claim 4 wherein vitamin A is provided as Vitamin A palmitate and β-carotene.

22. The supplement of claim 11 farther comprising docusate sodium.

\* \* \* \* \*